(12) United States Patent
Isaacson et al.

(10) Patent No.: US 12,109,374 B2
(45) Date of Patent: Oct. 8, 2024

(54) INTRAVENOUS THERAPY SYSTEM FOR BLOOD VESSEL ACCESS VIA A CURVED NEEDLE AND CURVED CATHETER

(71) Applicant: Becton, Dickinson and Company, Franklin Lakes, NJ (US)

(72) Inventors: S. Ray Isaacson, Layton, UT (US); Marc Weimer, South Jordan, UT (US); Andrew C. Farinella, Oradell, NJ (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 790 days.

(21) Appl. No.: 16/741,931

(22) Filed: Jan. 14, 2020

(65) Prior Publication Data
US 2020/0230364 A1 Jul. 23, 2020

Related U.S. Application Data

(60) Provisional application No. 62/794,431, filed on Jan. 18, 2019.

(51) Int. Cl.
| | |
|---|---|
| A61M 25/06 | (2006.01) |
| A61B 5/15 | (2006.01) |
| A61M 25/00 | (2006.01) |
| B21C 23/08 | (2006.01) |
| C21D 6/00 | (2006.01) |
| C21D 9/08 | (2006.01) |

(52) U.S. Cl.
CPC ... *A61M 25/0606* (2013.01); *A61B 5/150992* (2013.01); *A61M 25/001* (2013.01); *B21C 23/085* (2013.01); *C21D 6/004* (2013.01); *C21D 9/08* (2013.01)

(58) Field of Classification Search
CPC ............ A61M 25/0606; A61M 25/001; A61B 5/150992; B21C 23/085; C21D 6/004; C21D 9/08
USPC ........................................................ 604/164
See application file for complete search history.

(56) References Cited

U.S. PATENT DOCUMENTS

| | | | |
|---|---|---|---|
| 4,906,171 A | 3/1990 | Miller | |
| 6,899,721 B2 * | 5/2005 | Sferco | A61B 6/504 606/205 |
| 2011/0152836 A1 | 6/2011 | Riopelle et al. | |
| 2015/0112278 A1 | 4/2015 | Ray et al. | |
| 2016/0317350 A1 * | 11/2016 | Kadonosono | A61M 5/3297 |

FOREIGN PATENT DOCUMENTS

| | | |
|---|---|---|
| DE | 2403730 | 8/1974 |
| GB | 1243211 A | 8/1971 |
| GB | 2487527 | 8/2012 |

(Continued)

*Primary Examiner* — Phillip A Gray
(74) *Attorney, Agent, or Firm* — Kirton McConkie; Whitney Blair; Kevin Stinger

(57) ABSTRACT

An intravenous therapy system may include a curved needle; and a curved catheter formed around the outside surface of the curved needle; wherein, upon insertion of a first length of the curved needle and curved catheter into a patient's body, a curvature angle of the curved needle and curved catheter causes the curved needle and curved catheter to intersect axially with a blood vessel in the patient's body.

20 Claims, 10 Drawing Sheets

(56) References Cited

FOREIGN PATENT DOCUMENTS

| | | |
|---|---|---|
| JP | S59123636 | 7/1984 |
| JP | 2005341987 A | 12/2005 |
| JP | 2015119854 A | 7/2015 |
| WO | 98390401 W | 9/1998 |
| WO | 2018025967 A1 | 2/2018 |

* cited by examiner

INTRAVENOUS THERAPY SYSTEM FOR BLOOD VESSEL ACCESS VIA A CURVED NEEDLE AND CURVED CATHETER

RELATED APPLICATIONS

This application claims the benefit of U.S. Provisional Patent Application No. 62/794,431, filed Jan. 18, 2019, and entitled PRE-CURVED NEEDLE AND CATHETER, which is incorporated herein in its entirety.

BACKGROUND

Some intravenous therapy systems may include a straight needle and catheter axially formed around the straight needle. Intravenous therapy systems may be used for a variety of infusion therapies. For example, intravenous therapy systems may be used for infusing fluids, such as a saline solution, various medicaments, and parenteral nutrition, into a patient. intravenous therapy systems may also be used for withdrawing blood from the patient. To facilitate insertion into a body, the needle of the intravenous therapy system includes a distal tip that includes a bevel used to interface with a skin of a patient as the bevel faces away from skin of the patient.

There are several issues that occur with intravenous therapy systems that use straight needles, however. During operation of these intravenous therapy systems, the bevel formed on a distal end of the needle may cause the distal end of the needle to "dive" deeper into the patent even when the insertion angle of the intravenous therapy system remains constant. In order to complete the insertion process of the intravenous therapy system, the clinician may lower the angle of the intravenous therapy system relative to the patient so as to combat the needle diving further into the body of the patient. This may be done so as to attempt to also position the distal end of the needle in a more parallel position relative to the patient's blood vessel being accessed by the intravenous therapy system.

This maneuvering of the intravenous therapy system by the clinician, however, has limited effect in smaller gauge needles and catheters (e.g. 20-gauge, 22-gauge, and 24-gauge) because, as the gauge of the needle increases, the needle bends relatively easier when the insertion angle is lowered. The distal end of the needle may then be positioned at about a 20-degree angle within the vein and may not straighten out. Ultrasound images have shown that the angle of the intravenous therapy system within the patient's blood vessel places the distal end of the needle close to an interior surface of the blood vessel with the distal end of the needle digging into the back wall of the blood vessel. The distal end of the needle digging into the back wall of the patient's blood vessel may cause blood vessel trauma, inflammation, phlebitis, among other medical conditions. This is also an issue when drawing blood with the distal end of the needle suctioned against the vein wall when a vacuum within the intravenous therapy system is created. This creation of the vacuum may further cause the distal end of the needle to become clogged and, thereby prevent fluids to pass through the needle and/or catheter of the intravenous therapy system.

The subject matter claimed herein is not limited to embodiments that solve any disadvantages or that operate only in environments such as those described herein. Rather, this background is provided to describe an environment in which the presently described embodiments may operate.

SUMMARY

The present disclosure relates generally to intravenous therapy system and related systems and methods. In some embodiments, an intravenous therapy system provides for the access of a patient's blood vessels in such a way as to avoid any additional physical trauma to the patient apart from an initial insertion of the intravenous therapy system into the patient's blood vessel. The intravenous therapy system may include a curved needle.

In an embodiment, a curved catheter is formed around the outside surface of the curved needle. In an embodiment, a curved catheter is formed coaxially with the curved needle. In an embodiment, a curved catheter may be formed generally coaxially with the curved needle. Upon insertion of a first length of the curved needle and curved catheter into a patient's body, a curvature angle of the curved needle and curved catheter causes the curved needle and curved catheter to intersect axially with a blood vessel in the patient's body. By creating a curve in the needle and catheter of the intravenous therapy system, the insertion of the intravenous therapy system into the patient may cause the distal tip of the needle run parallel and axial with the blood vessel such that the distal end of the needle is not forced into an interior wall of the patient's blood vessel.

The present disclosure further relates to a method of manufacturing an intravenous device. The method may include, in some embodiments, introducing a heated metal at an extrusion die. In the embodiments presented herein, the extrusion die may include an internal spider die such that extruding the heated metal through the extrusion die forms a hollow tube therefrom. In these embodiments, the exit plane of the internal spider die is adjusted to be non-orthogonal to an extrusion axis of the spider die to form a curve in the hollow tube.

The present disclosure further relates to another method of manufacturing an intravenous therapy system. In an embodiment, the method includes introducing a heated metal at an extrusion die, wherein the extrusion die comprises an internal spider die. The method may also include extruding the heated metal through the extrusion die forming a hollow tube therefrom and forming a bevel at a distal end of the hollow tube. In these embodiments, the methods may include forming a plastic catheter around the outside surface of the curved metal. For example, the methods may include forming the plastic catheter coaxially with or generally coaxially with the curved metal. In some embodiments, the method may also include, with a bend fixture, bending the hollow tube and catheter to form a curve in the hollow tube and catheter.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1:
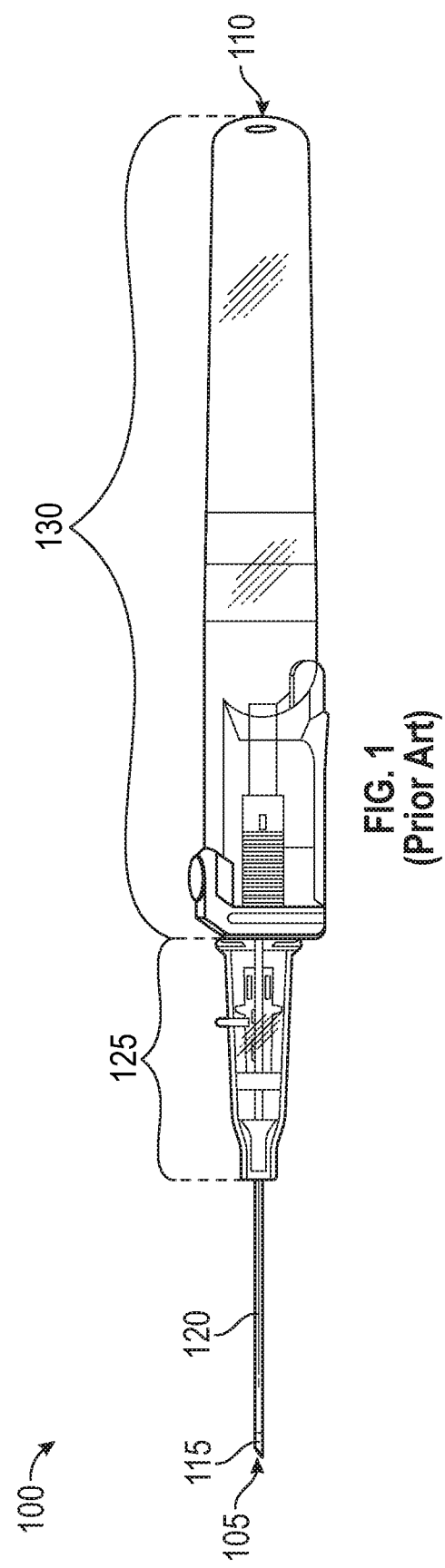
FIG. 1 is a side view of a prior art intravenous therapy system.

As used herein, the term "proximal" refers to a location on the needle of an intravenous therapy system that, during use, is closest to the clinician using the intravenous therapy system and farthest from the patient in connection with whom the device is used. Conversely, the term "distal" refers to a location on the needle of an intravenous therapy system that, during use, is farthest from the clinician using the intravenous therapy system and closest to the patient in connection with whom the intravenous therapy system is used.

As used herein, the term "top", "up" or "upwardly" refers to a location on the needle of this intravenous therapy system that, during use, is radially away from the longitudinal axis of the intravenous therapy system and away from the patient's skin. Conversely, as used herein, the term "bottom", "down" or "downwardly" refers to a location on the needle of this intravenous therapy system that, during use, is radially away from the longitudinal axis of the device and toward the patient's skin.

As used herein, the term "in" or "inwardly" refers to a location with respect to the needle of this intravenous therapy system that, during use, is toward the inside of the intravenous therapy system. Conversely, as used herein, the term "out" or "outwardly" refers to a location with respect to the needle of this intravenous therapy system that, during use, is toward the outside of the intravenous therapy system.

This invention is described herein using like reference numbers for like elements in the different embodiments. Although the embodiments described herein are used in connection for use as an intravenous therapy system to receive a blood sample or introduce a medicament into the body of a patient, it is to be understood that this intravenous therapy system is applicable to other medical devices where it is desirable for a needle and/or catheter to be inserted into a blood vessel of a patient. In addition, while the embodiments of the intravenous therapy system are satisfied by embodiments in many different forms, there are shown in the drawings and herein described in detail, preferred embodiments of the invention with the scope of the disclosure measured by the appended claims.

FIG. 1 is a side view of a prior art intravenous therapy system 100. The intravenous therapy system 100, as depicted, show a straight needle 115. The intravenous therapy system 100 may also include a straight catheter 120 formed around an exterior surface of the straight needle 115. The straight catheter 120 may be formed coaxially with or generally coaxially with the straight needle 115. A hub 125 may be coupled to the straight needle 115 and straight catheter 120. Upon insertion of the straight needle 115 and straight catheter 120 into the blood vessel of a patient, the straight needle 115 may be axially removed from within the straight catheter 120. The intravenous therapy system 100 of the prior art may also include a barrel 130 coupled to the hub 125.

The intravenous therapy system 100 may include a proximal end 110 that a clinician or other health care provider (HCP) may hold in order to insert the intravenous therapy system 100 into a patient's body. The intravenous therapy system 100 may also include a distal end 105 opposite the proximal end 110 where a tip of the straight needle 115 is located. At the distal end 105 of the straight needle 115, a bevel may be formed. The bevel may be an inclined cut formed at the tip of the straight needle 115 that creates a pointed edge at the very most distal end 105 of the straight needle 115.

Figure 2:
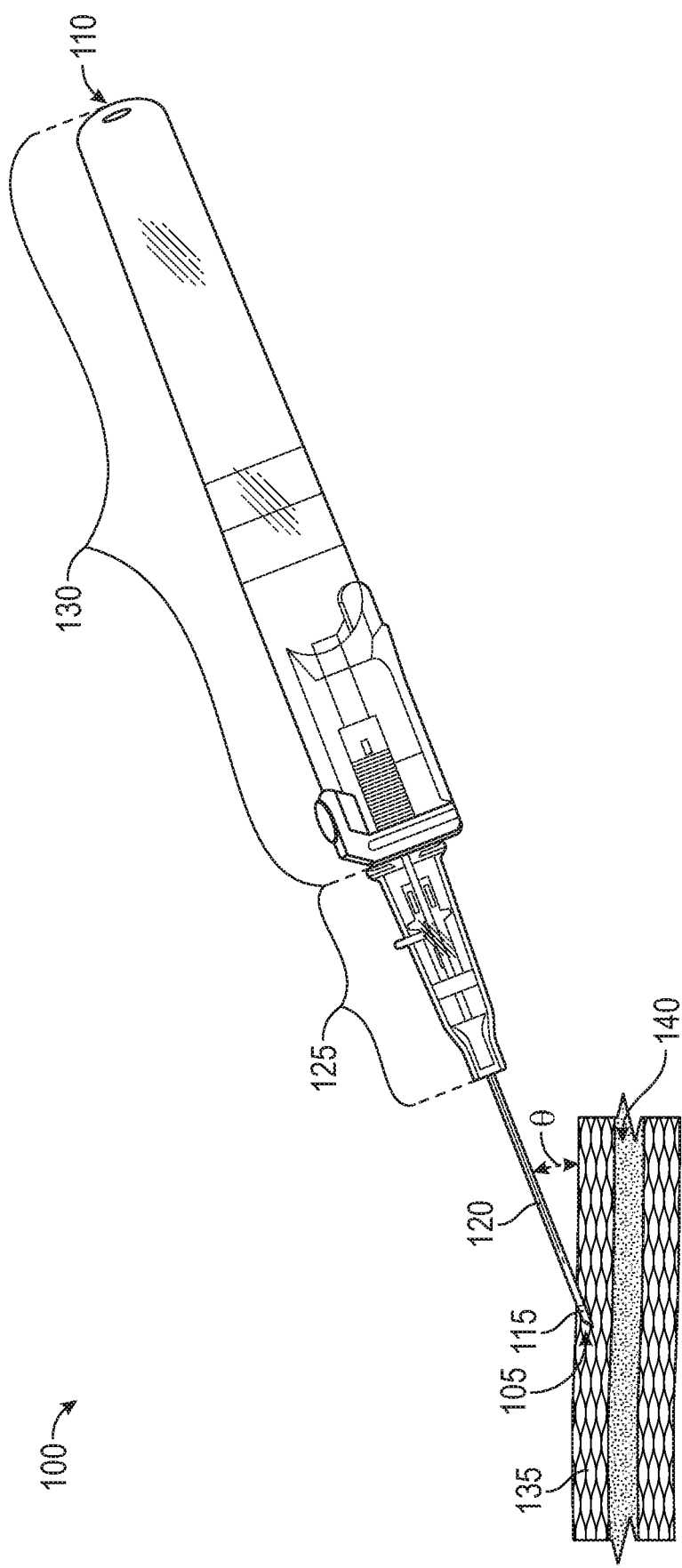
FIG. 2 is a side view of a prior art intravenous therapy system.

FIG. 2 is a side view of a prior art intravenous therapy system 100. FIG. 2 shows the intravenous therapy system 100 of FIG. 1 being inserted into a patient's body 135 with the body including a blood vessel 140. The intravenous therapy system 100 may pierce the skin of a patient at a first angle θ of the intravenous therapy system 100 relative to the patient's body 135.

Figure 3:
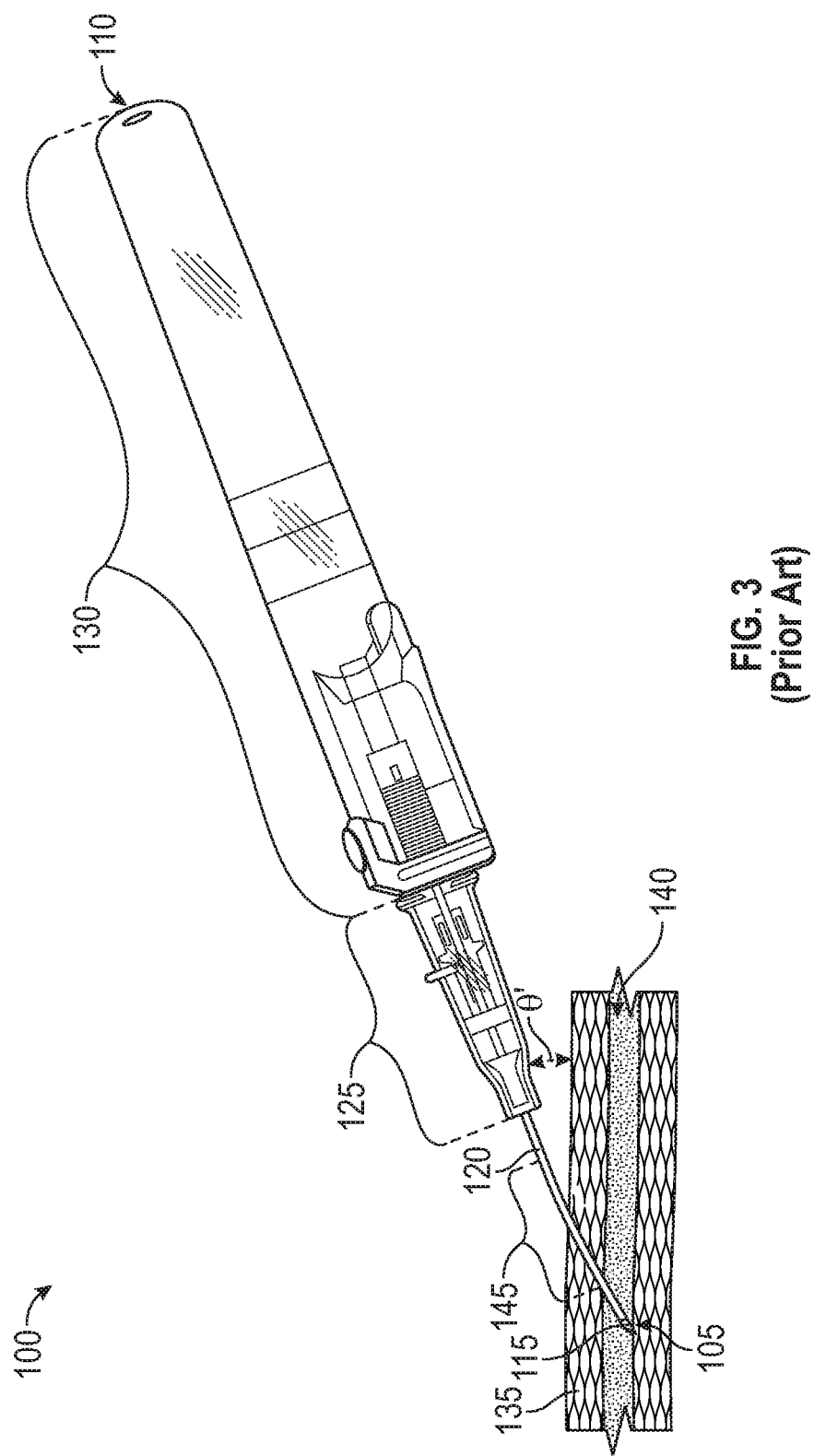
FIG. 3 is a side view of a prior art intravenous therapy system.

FIG. 3 is a side view of a prior art intravenous therapy system 100. FIG. 3 shows the intravenous therapy system 100 after it has punctured a wall of the blood vessel 140 within the patient's body 135. As a result of the bevel formed at the distal end 105 of the straight needle 115, the straight needle 115 and straight catheter 120 may tend to "dive" down into the patient's body at an angle different than the angle θ shown in FIG. 2. In order to prevent this from occurring, a clinician or other HCP may adjust the approach angle of the intravenous therapy system 100 by decreasing the angle of the barrel 130 of the intravenous therapy system 100 to a new and shallower angle θ'. Such a maneuver may cause additional issues with related to the insertion of the intravenous therapy system 100. For example, especially with smaller gauges of straight needles 115 and straight catheters 120, the straight needle 115 and straight catheter 120 may bend under the pressure created between the patient's skin and the new angle θ' of the barrel 130 relative to the patient's body 135. Even further, the adjustment of the approach angle of the intravenous therapy system 100 relative to the patient's body 135 does not actually prevent the distal end 105 of the straight needle 115 from diving further into the patient's body 135. Instead, the further advancement of the straight needle 115 and straight catheter 120 of the intravenous therapy system 100 into the patient's body 135 by the clinician may cause the distal end 105 of the straight needle 115 to puncture an opposite sidewall of the blood vessel 140.

Figure 4:
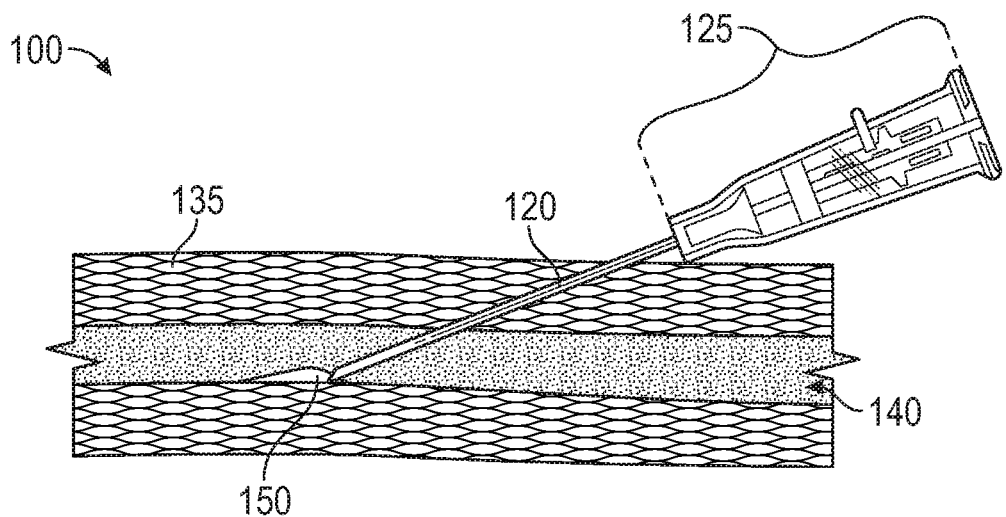
FIG. 4 is a side view of a prior art intravenous therapy system.

FIG. 4 is a side view of a prior art intravenous therapy system 100. In FIG. 4, the straight needle 115 formed around the straight catheter 120 has been removed leaving the straight catheter 120 therein. The straight needle 115 may be formed coaxially with or generally coaxially with the straight catheter 120. Because of the placement of the straight needle 115 as depicted in FIG. 3 causes the distal end 105 of the straight needle 115 to be placed next to the wall of the blood vessel 140, a distal end of the straight catheter 120 remains close to the wall of the blood vessel 140 when the straight needle 115 is removed. As such, the hollow portion of the straight catheter 120 may be prevented from receiving or passing a fluid therethrough due to the tip of the straight catheter 120 being blocked by the wall of the blood vessel 140. In an example where blood is to be drawn from within the blood vessel 140, any disparities in pressure between the interior of the hollow portion of the straight catheter 120 and the interior of the blood vessel 140 may cause a vacuum to form at the distal end of the straight catheter 120 thereby causing the straight catheter 120 to be suctioned onto the interior surface of the walls of the blood vessel 140.

The intravenous therapy system 100 of the prior art as formed may, therefore, prevent proper insertion of the intravenous therapy system 100 into a patient's blood vessel 140. Instead, such an insertion of the intravenous therapy system 100 described in connection with FIGS. 1-4 may cause vein irritation, phlebitis and result in poor blood draws or infusions into the blood.

Figure 5:
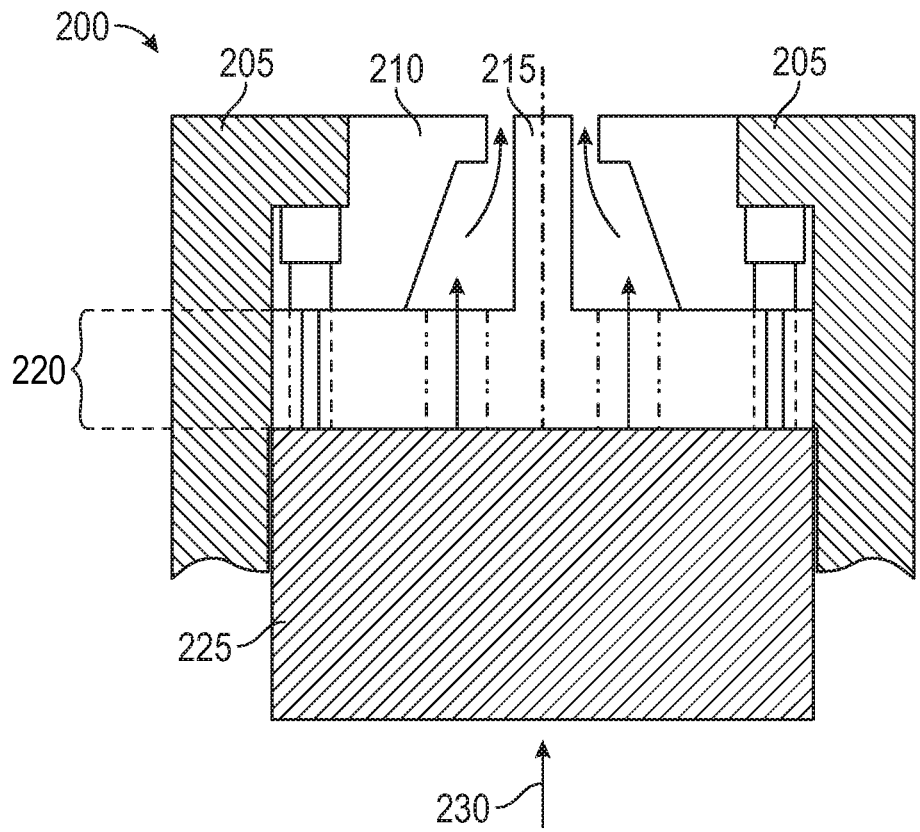
FIG. 5 is a side cross-sectional view of a prior art extrusion die used to form an intravenous therapy system.

FIG. 5 is a side cross-sectional view of a prior art extrusion die 200 used to form an intravenous therapy system. The extrusion die 200 may include an extrusion barrel 205 into which a spider die 220 may be placed. The spider die 220 may be made of a material that can withstand an amount of pressure pressed against it from behind by a heated metal billet 225 being pressed against the spider die 220 by a ramming device (not shown). As such, the spider die 220 is made of a hardened metal such as hardened steel.

During operation of the extrusion die 200, the heated metal billet 225 is placed behind the spider die 220 and rammed into and through the spider die 220 by the ramming device described. The amount of pressure applied to the heated metal billet 225 may be dependent on the temperature of the heated metal billet 225, the volume of the heated metal billet 225, and the pressure applied to the heated metal billet 225 by the ramming device.

As a result of pressure being applied to the heated metal billet 225, the metal of the heated metal billet 225 is forced through the spider die 220 and funneled around a central shaft 215 of the spider die 220. The central shaft 215 may be sized to define the interior diameter of the hollow tube (e.g., a precursor form of the straight needle 115 of FIGS. 1-3) formed by the extrusion die 200. The spider die 220 may also include a funnel 210 or other interior surface that defines an outer diameter of the of the hollow tube (e.g., a precursor form of the straight needle 115 of FIGS. 1-4) formed by the extrusion die 200. As a result of the shape of the spider die 220, a hollow tube may be formed and exit out of an end of the extrusion die 200 that may serve as a precursor to the straight needle 115 as described as being used in FIGS. 1-4.

As shown in FIG. 5, the exiting plane of the spider die 220 is orthogonal to an axis of the central shaft 215. This orientation of the central shaft 215 relative to the exiting plane of the spider die 220 causes the extrusion die 200, during operation, to create a straight hollow pipe that is used to form the straight needle. As described herein, however, a straight needle as shown in FIGS. 1-4 may cause vein irritation, phlebitis and result in poor blood draws or infusions into the blood.

Figure 6:
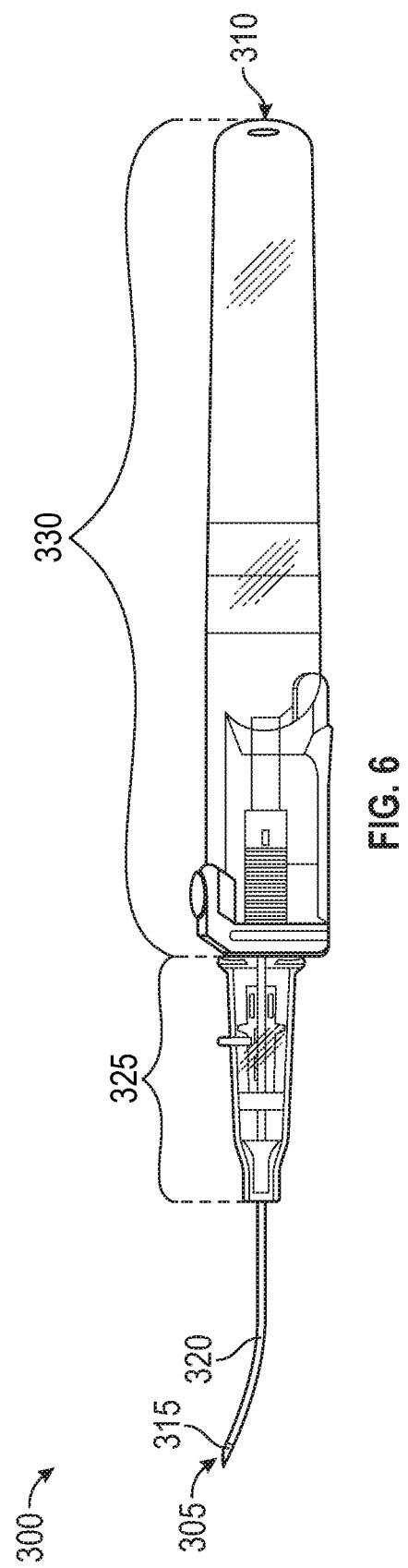
FIG. 6 is a side view of an intravenous therapy system according to an embodiment of the present disclosure.

FIG. 6 is a side view of an intravenous therapy system 300 according to an embodiment of the present disclosure. The intravenous therapy system 300 described herein may include a distal end 305 and a proximal end 310. In an embodiment, the proximal end 310 may be held by a clinician or other HCP in order to orient the intravenous therapy system 300 relative to a blood vessel within a patient's body.

At a proximal end 310 of the intravenous therapy system 300, the intravenous therapy system 300 may include a barrel section 330. In an embodiment, the barrel section 330 may be any device that may be coupled to a hub section 325 of the intravenous therapy system 300. In an embodiment, the barrel section 330 may be a blood sample vial to receive a blood sample from a patient when the intravenous therapy system 300 has accessed a blood vessel within the patient's body. In another embodiment, the barrel section 330 may be a disposable device that is meant to be temporarily coupled to the hub section 325 for ease of access by a clinician during insertion of the intravenous therapy system 300 into the body of the patient. Although the present disclosure provides specific examples of what the barrel section 330 is and its functions, these are meant to be non-limiting examples and the present disclosure contemplates that any device may be coupled to the hub section 325 to serve a specific purpose or function.

The hub section 325 may include any type of coupling device that allows the hub section 325 to be coupled to any device to receive or provide a fluid to the hub section 325 and through a curved needle 315 and curved catheter 320. In an embodiment, the hub section 325 may include a number of threads that may interface with any type of device used to pass a fluid through the hub section 325.

In an embodiment, the hub section 325 may be physically coupled to a curved catheter 320. In an embodiment, the curved catheter 320 may include a straight or non-curved tube that is curved in response to insertion of the curved needle 315 through the straight or non-curved tube during assembly or manufacture. In an embodiment, the curved catheter 320 may be made of any type of resilient material that is resilient to the curved catheter 320 being pinched or caving in on itself while the curved catheter 320 is in the patient's body. In an embodiment, the curved catheter 320 may be made of a polymer or another suitable material.

The intravenous therapy system 300 may, in an embodiment, include a curved needle 315 formed at a distal end 305 of the intravenous therapy system 300. The curved needle 315 may be formed within the curved catheter 320 and extend around the curved catheter 320 along the entire length of the curved needle 315. The curved needle 315 may be formed within the curved catheter 320 and may extend coaxially or generally coaxially with the curved catheter 320 along the entire length of the curved needle 315. In a specific example, the curved needle 315 is longer than the curved catheter 320 so as to have a distal end of the curved needle 315 extending beyond, for a distance, the curved catheter 320. The curved needle 315 may also include a bevel formed at the distal end of the curved needle 315. The bevel may be formed so as to bring the distal end of the curved needle 315 to a sharp point. The sharp point of the bevel may allow for the easy insertion of the curved needle 315 into a patient's body. In an embodiment, the curved needle 315 is made of a stainless steel or other type of metal that does not interact chemically with the fluids and tissues within the patient's body. Thus, although specific examples are provided herein describing the curved needle 315 as being made of stainless steel, the curved needle 315 may be made of other types of metal as would suit a particular medical purpose.

The curved catheter 320 and curved needle 315 have a level of curvature that allows for relatively easier insertion and indwelling of the intravenous therapy system 300 into and within the patient's body. In contrast to the intravenous therapy system of the prior art described in connection with FIGS. 1-4, the curvature of the curved catheter 320 and curved needle 315 may be such that, upon insertion into the patient's body, the curvature of the curved catheter 320 and curved needle 315 provides for the distal end of the curved needle 315 to follow parallel with a blood vessel within the patient.

Figure 7:
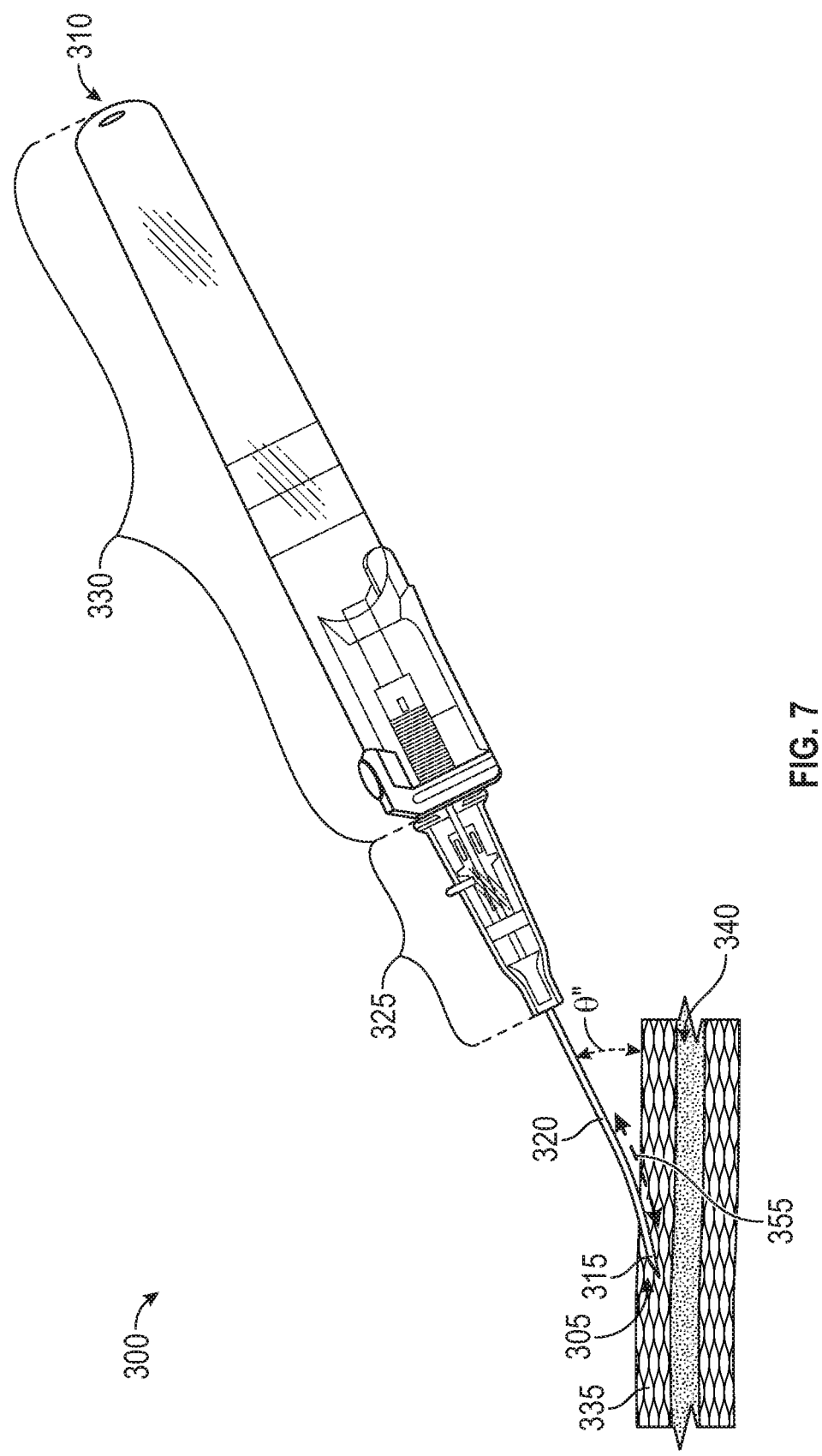
FIG. 7 is a side view of an intravenous therapy system according to an embodiment of the present disclosure.
Figure 8:
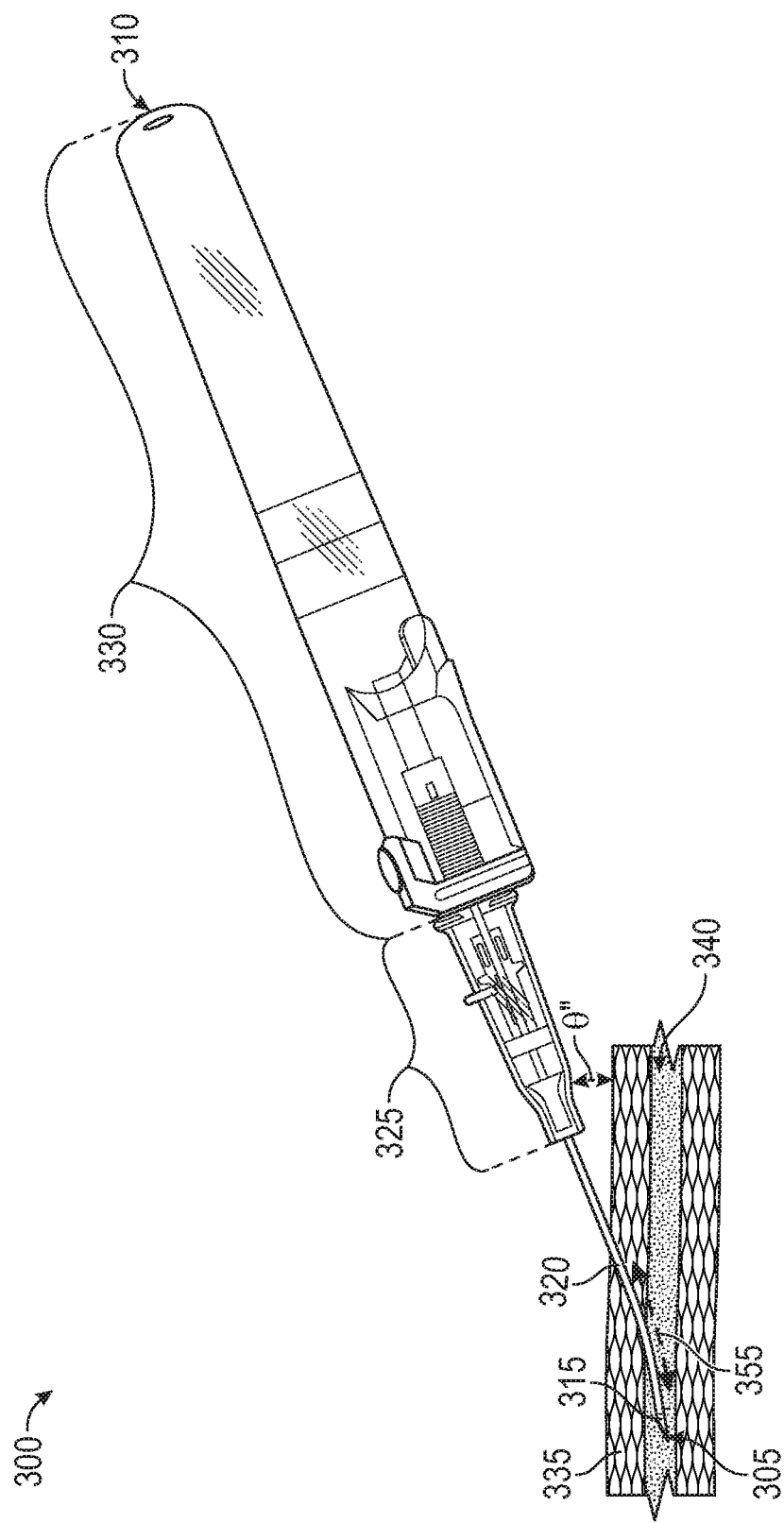
FIG. 8 is a side view of an intravenous therapy system according to an embodiment of the present disclosure.
Figure 9:
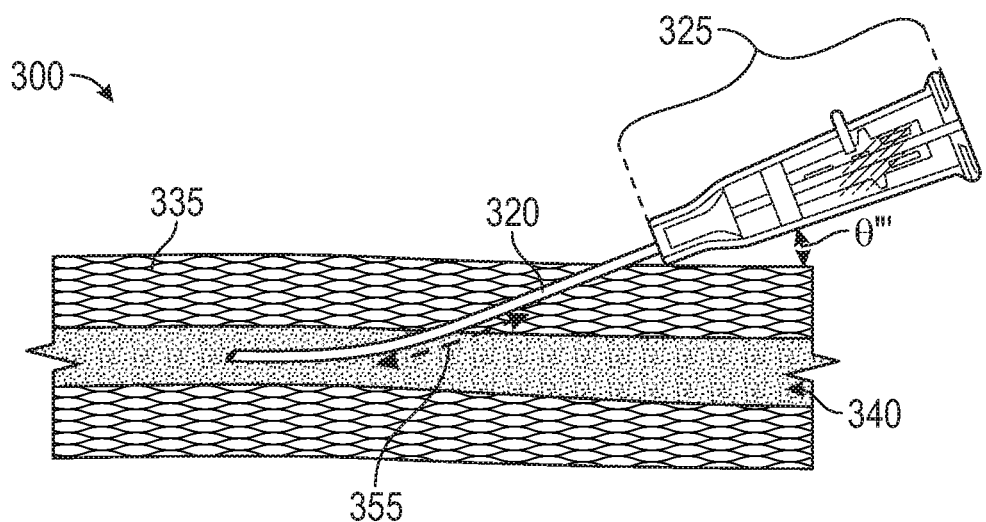
FIG. 9 is a side view of an intravenous therapy system according to an embodiment of the present disclosure.

FIGS. 7-9 show a progression of an insertion of the intravenous therapy system 300 described in connection with FIG. 6. FIG. 7 is a side view of an intravenous therapy system 300 according to an embodiment of the present disclosure. As described in connection with FIG. 6, the intravenous therapy system 300 may include a barrel section 330 and a hub section 325. In an embodiment, the barrel section 330 may be any device that may be coupled to a hub section 325 of the intravenous therapy system 300. In an embodiment, the barrel section 330 may be a blood sample vial to receive a blood sample from a patient when the intravenous therapy system 300 has accessed a blood vessel within the patient's body. In another embodiment, the barrel section 330 may be a disposable device that is meant to be temporarily coupled to the hub section 325 for ease of access by a clinician during insertion of the intravenous therapy system 300 into the body of the patient. Although the present disclosure provides specific examples of what the barrel section 330 is and its functions, these are meant to be non-limiting examples and any device may be coupled to the hub section 325 to serve a specific purpose or function.

The hub section 325 may include any type of coupling device that allows the hub section 325 to be coupled to any device to receive or provide a fluid to the hub section 325 and through a curved needle 315 and curved catheter 320. In an embodiment, the hub section 325 may include a number of threads that may interface with any type of device used to pass a fluid through the hub section 325.

During operation of the intravenous therapy system 300, a clinician may hold the intravenous therapy system 300 in the clinician's hand at, for example, the barrel section 330 of the intravenous therapy system 300. In an embodiment, the clinician may insert the intravenous therapy system 300 at a first angle θ" relative to the patient's body 335. In an embodiment, this angle θ" may be larger than an insertion angle θ of an intravenous therapy system 300 having a straight needle and straight catheter shown in FIG. 2 of the prior art.

As a result of this relatively larger first angle θ", the curvature of the curved needle 315 and curved catheter 320 may automatically curve into a blood vessel upon insertion into the patient's body. This first angle θ" allows the curved needle 315 and curved catheter 320 to follow a trajectory within the patient's body so as to run parallel to the patient's blood vessel 340.

In order to achieve this insertion, the curvature 355 of the curved catheter 320 and curved needle 315 may be sufficient so as to, upon full insertion into the patient's body, the curved needle 315 and curved catheter 320 lies axially within a target blood vessel. In an embodiment, the curvature 355 of the curved needle 315 and curved catheter 320 may have a curvature angle of between 5 and 15 degrees. The angle of the curvature 355 may be measured from the distal end of the curved needle 315 to an axis of the hub section 325, in an embodiment.

The curved needle 315 may include a bevel formed at a distal end of the curved needle 315. The bevel may be formed so as to bring the distal end of the curved needle 315 to a shape point. The sharp point of the bevel may allow for the easy insertion of the curved needle 315 into a patient's body. In an embodiment, an edge of the bevel is formed to face towards a center point of the curvature 355 such that, during insertion of the intravenous therapy system 300 into the patient's body, the bevel is facing away from the patient's body.

FIG. 8 is a side view of an intravenous therapy system 300 according to an embodiment of the present disclosure. FIG. 8 shows the intravenous therapy system 300 inserted fully or nearly fully into the patient's body 335 and into a blood vessel 340. In FIG. 8, the curved needle 315 and curved catheter 320 has followed the curve formed by the curved needle 315 and curved catheter 320 similar to that experienced by clinicians and other HCP using a surgical stitching needle.

During insertion of the intravenous therapy system 300, the curved needle 315 and curved catheter 320 may use the curvature 355 created in the curved needle 315 and curved catheter 320 to pass through a portion of the patient's body 335, into a blood vessel 340, and follow, co-axially, with the blood vessel 340. During insertion into the blood vessel 340, the clinician may reduce the angle θ" of the intravenous therapy system 300 relative to the patient's body 335 so that the curved insertion point created by the curved needle 315 and curved catheter 320 is used to direct the curved needle 315 further into the blood vessel 340 without puncturing an opposite wall of the blood vessel 340. The use of the intravenous therapy system 300 prevents the distal end of the curved needle 315 from continuing through the blood vessel 340 thereby damaging the blood vessel and other structures within the patient's body 335.

FIG. 9 is a side view of an intravenous therapy system 300 according to an embodiment of the present disclosure. In FIG. 9, the curved needle 315 and barrel section 330 have been removed and the curved catheter 320 is left to remain within the blood vessel 340 of the patient. The curvature of the curved catheter 320 may be maintained as a result of a thermo-heating process conducted on the curved catheter 320 when it was installed around the curved needle 315. Because of the curvature of the curved needle 315, the distal end of the curved catheter 320 may be coaxial with a longitudinal axis or length of a portion of the blood vessel 340. In this position within the blood vessel 340, the curved catheter 320 may be able to draw a blood sample or administer a medicament, for example, without being placed against a wall of the blood vessel 340.

FIG. 9 shows that the angle θ''' of the hub section 325 relative to the patient's body 335 has been reduced. This angle θ''' may be sufficient to allow the hub section 325 to be affixed to the patient's body 335 for immediate and subsequent blood draws and infusions. The hub section 325 may be affixed to the patient's body 335 using any medical tape, for example, so as to secure the hub section 325 to the patient's body 335 and maintaining the curved catheter 320 within the patient's blood vessel 340. The hub section 325 may include a number of threads formed at a proximal end of the hub section 325 to receive other medical devices such as an intravenous lead or a syringe.

The intravenous therapy system 300 described in connection with FIGS. 6-9 improves the difficulties associated with and experienced by clinicians using a straight needle and straight catheter system. The presently described intravenous therapy system 300 improves the success of a first "stick" or insertion of the intravenous therapy system 300 by a clinician by automatically steering the intravenous therapy system 300 into the blood vessel 340 in such a position that is more parallel to the blood vessel 340. The intravenous therapy system 300 further reduces trauma on the blood vessel 340 thereby reducing blood vessel 340 wall irritation, inflammation and reducing phlebitis and occlusions. The intravenous therapy system 300 also increases the likelihood of a successful blood draw from the intravenous therapy system 300 by a clinician or other HCP reducing the number of attempts to conduct the blood draw or infusion of medicaments.

Figure 10:
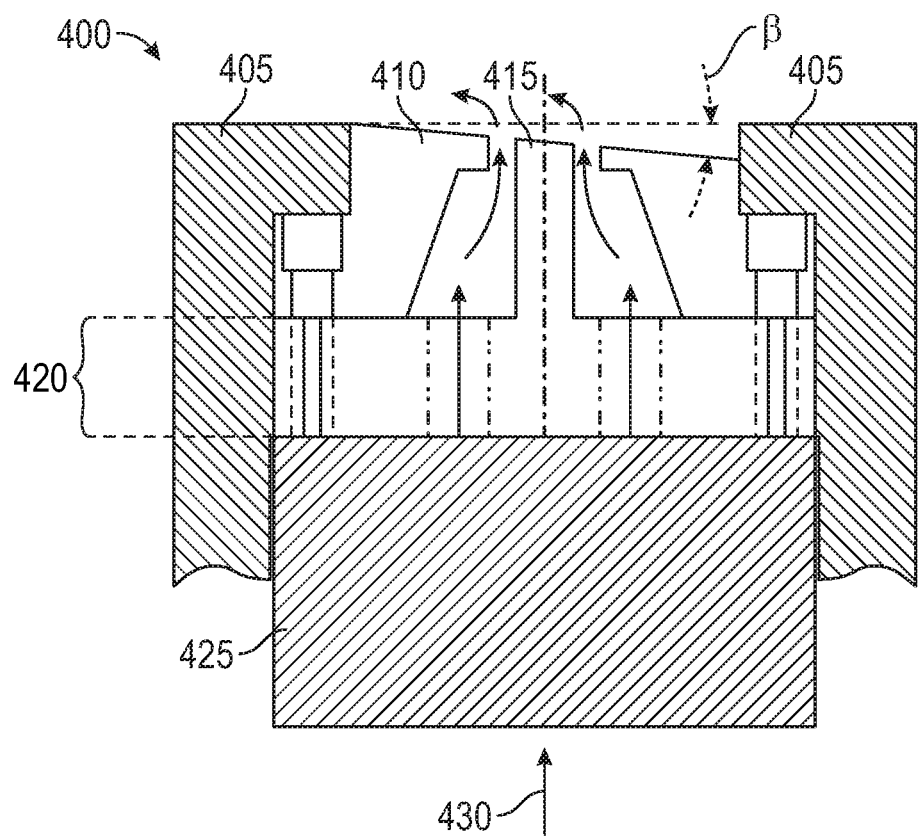
FIG. 10 is a side cross-sectional view of an extrusion die used to manufacture an intravenous therapy system according to an embodiment of the present disclosure.

FIG. 10 is a side cross-sectional view of an extrusion die 400 used to manufacture an intravenous therapy system according to an embodiment of the present disclosure. The extrusion die 400 may include an extrusion barrel 405 into which a spider die 420 may be placed. The spider die 420 may be made of a material that can withstand an amount of pressure pressed against it from behind by a heated metal billet 425 being pressed against the spider die 420 by a ramming device (not shown). As such, the spider die 420 is made of a hardened metal such as hardened steel.

During operation of the extrusion die 400, the heated metal billet 425 is placed behind the spider die 420 and rammed into and through the spider die 420 by the ramming device described. The amount of pressure applied to the heated metal billet 425 may be dependent on the temperature of the heated metal billet 425, the volume of the heated metal billet 425, and the pressure applied to the heated metal billet 425 by the ramming device.

As a result of pressure being applied to the heated metal billet 425, the metal of the heated metal billet 425 is forced through the spider die 420 and funneled around a central shaft 415 of the spider die 420. The central shaft 415 may be sized to define the interior diameter of the hollow tube (e.g., a precursor form of the curved needle 315 of FIGS. 6-8) formed by the extrusion die 400. The spider die 420 may also include a funnel portion 410 or other interior surface that defines an outer diameter of the of the hollow tube (e.g., a precursor form of the curved needle 315 of FIGS. 6-8) formed by the extrusion die 400. During the application of pressure to the heated metal billet 425, the metal of the heated metal billet 425 may follow the arrows passing through the orifices formed in the spider die 420 and the exit orifice of the spider die 420. As a result of the shape of the spider die 420, a hollow tube may be formed and exit out of an end of the extrusion die 400 that may serve as a precursor to the curved needle 315 as described as being used in FIGS. 6-8.

As shown in FIG. 10, the exiting plane of the spider die 420 is non-orthogonal to an axis of the central shaft 415. This is in contrast to the exit plane as described in connection with the prior art extrusion die shown in FIG. 5. This non-orthogonal orientation of the exiting plane relative to the central shaft 415 of the spider die 420 causes the extrusion die 200, during operation, to create a curved hollow pipe that is used to form the curved needle 315 described in connection with FIGS. 6-8. The curvature (355 in FIGS. 7 and 8) of the curved needle may be dependent on the angle β of the exiting plane of the spider die 420 and the speed of the extrusion of the metal out of the extrusion die 400, among other manufacturing variables. During operation of the extrusion die 400, as the exiting metal passes a lowered edge of the exiting plane of the spider die 420 the metal may be made to curve along the lines depicted in the figure resulting from the fluidic properties of the metal and the mechanical stresses applied to that portion of the exiting metal relative to the metal still passing through the interface between the funnel portion 410 and the axis of the central shaft 415 of the spider die 420. As a result, the forming hollow pipe causes the metal passing through the lower part of the exiting plane of the spider die 420 to curve away from that lowest part of the exiting plane of the spider die 420 and towards the relatively higher side of the exiting plane.

In an embodiment, the exiting plane of the spider die 420 may be made to change orientation as the metal passes through the spider die 420. In this embodiment, the orientation of the funnel portion 410 of the spider die 420 may be allowed, via hydraulics for example, to be oriented from a first angle β to an angle that is orthogonal to the axis of the central shaft 415. In this embodiment, the length and tip of the central shaft 415 may be altered to allow of the deformation of the metal according to the operation of the extrusion die 400 in the present embodiment. As the metal is extruded out of the spider die 420 of the extrusion die 400, the exiting plane may be maintained at the angle β for a specific length of the forming hollow tubing. The exiting plane may then be altered to decrease the angle of the exiting plane of the spider die 420 to be orthogonal to the axis of the central shaft 415. This change in the angle β results in the hollow tube being formed straight for a length of the forming hollow tube. As a result, a hollow tube may be formed that includes a curved section having a curvature 355 and a straight portion.

In any embodiment described herein, the method of manufacturing the curved needle 315 may include forming a catheter over the curved needle 315 to form a curved catheter 320 thereon. The curved catheter 320 may be made of a polymer that may be slid axially around the curved needle 315. In order to set the curvature of the curved catheter 320, the catheter may be subjected to a thermoforming process so that the curved catheter 320 may remain curved when the curved needle 315 is axially removed from the curved catheter 320.

Additionally, in any embodiment a bevel may be formed at a distal end of the curved needle 315. The bevel may be formed by a grinding process or any other material removal process. The bevel may be used to create a point that more comfortably pass into the patient's body.

Figure 11:
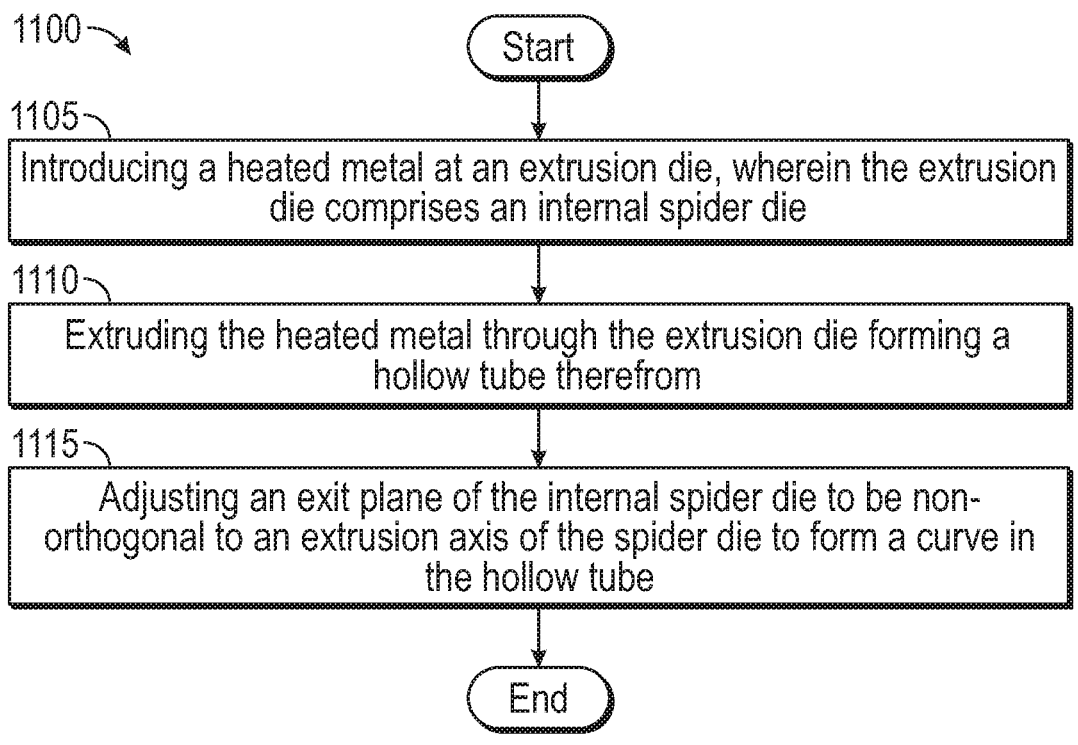
FIG. 11 is a flowchart depicting a method of manufacturing an intravenous therapy system according to some embodiments of the present disclosure.

FIG. 11 is a flowchart depicting a method 1100 of manufacturing an intravenous therapy system according to some embodiments of the present disclosure. The method 1100 may include, at block 1105, introducing a heated metal at an extrusion die, wherein the extrusion die comprises an internal spider die. As described herein, the spider die includes a number of extrusion holes that lead to a funnel portion 410. Although the present disclosure describes that the extrusion die includes a spider die, the present disclosure contemplates that other types of dies may be used to form the curved hollow tubes used to form the curved needle described herein.

The method 1100 may further include extruding the heated metal through the extrusion die forming a hollow tube therefrom, at block 1110. The heated metal may be extruded through the spider die of the extrusion die using a ramming device of any kind. Certain parameters of the extrusion process may be controlled so as to create the curvature of the curved needle. These parameters may include the amount of pressure placed on the heated metal billet by the ramming device, the temperature of the heated metal billet, the type of metal being extruded, a cross section volume of the various conduits formed through the spider die and the funnel portion of the spider die, among other parameters.

The method 1100 may further include adjusting, at block 1115, an exit plane of the internal spider die to be non-orthogonal to an extrusion axis of the spider die to form a curve in the hollow tube. As described herein, the angle (angle β in FIG. 10) of the exiting plane of the spider die (e.g., the exiting plane of the funnel portion of the spider die) may be adjusted to create a curvature of a hollow tube being extruded. This adjustment of the exiting plane may be maintained throughout the entire duration of forming the curved needle in an embodiment. In another embodiment, the exiting plane may be adjusted from a first angle to a second angle that is orthogonal to the axis of the central shaft.

Figure 12:
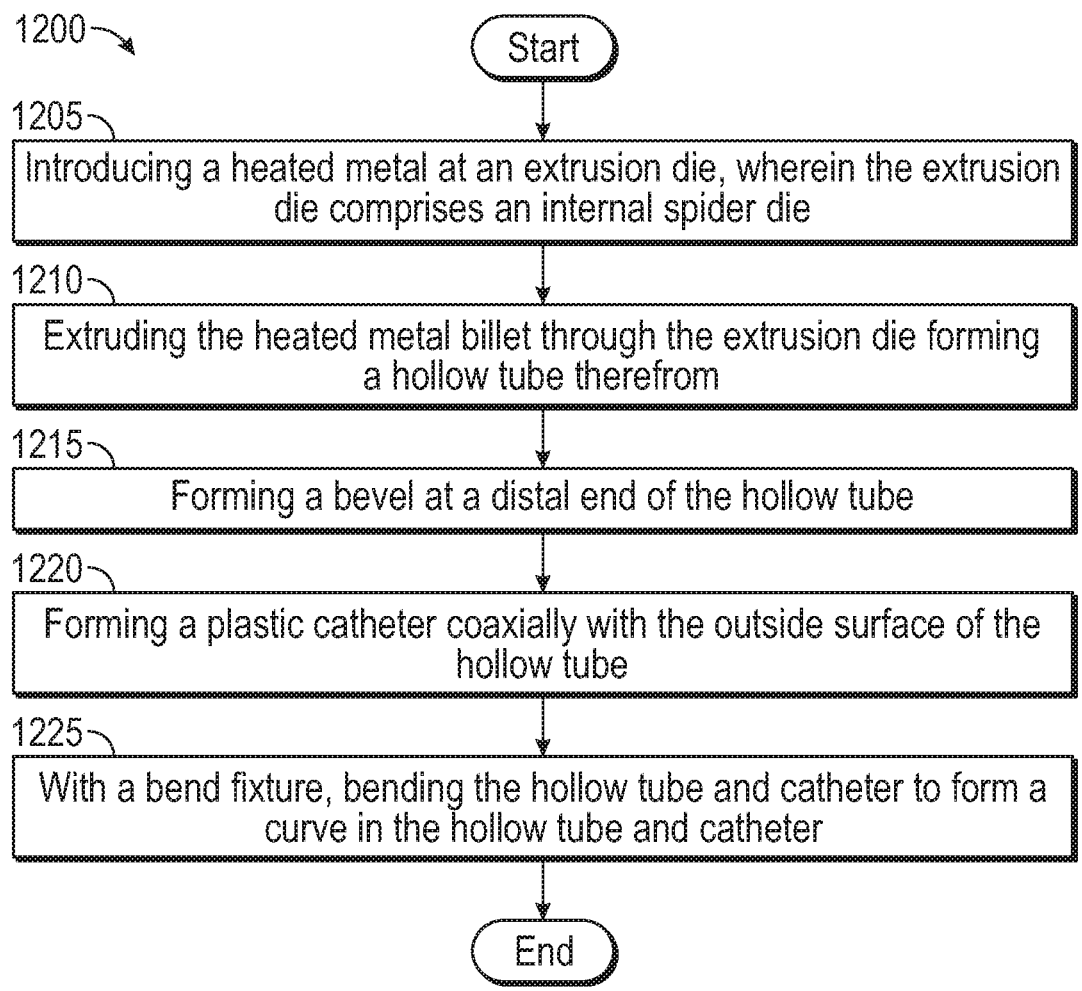
FIG. 12 is a flowchart depicting a method of manufacturing an intravenous therapy system according to an embodiment of the present disclosure.

FIG. 12 is a flowchart depicting a method 1200 of manufacturing an intravenous therapy system according to an embodiment of the present disclosure. The method 1200 may include, at block 1205, introducing a heated metal at an extrusion die, wherein the extrusion die comprises an internal spider die. The heated billet may be made of any metal and may be heated to any temperature sufficient to allow the metal to be pressed through the extrusion die.

The method 1200 may further include, at block 1210, extruding the heated metal billet through the extrusion die forming a hollow tube therefrom. The hollow tube, in an embodiment, may be a precursor form of the curved needle as described herein.

The method 1200 may also include forming a bevel at a distal end of the hollow tube at block 1215. The bevel may be created so as to allow the distal end of the needle to pass through the body of a patient and into a blood vessel (e.g., a vein).

The method 1200 may proceed at block 1220 with forming a plastic catheter around the outside surface of the metal. In some embodiments, the plastic catheter may be formed around the outside surface of the metal such that the plastic catheter is coaxial with or generally coaxial with the metal. The catheter, in an embodiment, may be physically coupled to a hub section of the intravenous therapy system via sonic welding or any other type of coupling process or device. In a specific embodiment, the needle may be fed through the catheter so that a distal end of the curved needle protrudes out from a distal end of the catheter.

The method 1200 may further include, at block 1225, bending the hollow tube and catheter to form a curve in the hollow tube and catheter. The curvature of the curve formed in the hollow needle and catheter may be dependent on the type of medical process the curved needle and curved catheter are being used for. In an embodiment, the curvature 355 of the curved needle 315 and curved catheter 320 may have a curvature angle of between 5 and 15 degrees.

The method 1200, in some embodiments, may include subjecting the installed curved catheter to a thermo-heating or thermoforming process. This may be done so that the curved catheter may remain curved when the curved needle is axially removed from the curved catheter.

The embodiments described herein provide for an intravenous therapy system that includes a curved needle. In an embodiment, a curved catheter is formed around an outer surface of the curved needle. In an embodiment, a curved catheter is formed coaxially with or generally coaxially with the curved needle. Upon insertion of a first length of the curved needle and curved catheter into a patient's body, a curvature angle of the curved needle and curved catheter causes the curved needle and curved catheter to intersect axially with a blood vessel in the patient's body. By creating a curve in the needle and catheter of the intravenous therapy system, the insertion of the intravenous therapy system into the patient may cause the distal tip of the needle run parallel and axial with the blood vessel such that the distal end of the needle is not forced into an interior wall of the patient's blood vessel.

Again, it is understood that the embodiments of the present application may be combined. As an example, the embodiments of FIGS. 1-12 may be arranged to fit specific uses based on the type of action being conducted. For example, where an artery is to be accessed by the needle, the information handling system may indicate, via the indicator system, a location of the artery while avoiding any veins. This may allow for the introduction of certain medicaments into a specific location in the patient's body without concern for that medicament being distributed throughout the patient's body.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosed embodiments.

The invention claimed is:

1. An intravenous therapy system, comprising:
   a hub section, comprising a top and a bottom opposite the top, wherein the bottom is configured to be proximate skin of a patient when the intravenous therapy system is inserted into a blood vessel, wherein the top of the hub section comprises a tab extending in an upward direction;
   a curved needle comprising a curve having a distal end of the curve spaced apart from a proximal end of the curve, wherein the proximal end of the curve is proximate a straight proximal end of the curved needle, wherein the curve is between 5 and 15 degrees with respect to the straight proximal end of the curved needle, wherein the curve is curved towards the upward direction; and
   a curved catheter, wherein the curved needle extends through the curved catheter;
   wherein, in response to insertion of a first length of the curved needle and a first length of the curved catheter into a patient's body, a curvature angle of the curved needle and the curved catheter causes the curved needle and the curved catheter to intersect axially with a blood vessel in the patient's body, wherein the curvature angle of the needle and the catheter is between 5 and 15 degrees.

2. The intravenous therapy system of claim 1, wherein the first length of the curved needle is longer than the first length of the curved catheter.

3. The intravenous therapy system of claim 1, the curved needle further comprising a bevel formed at a distal end of the curved needle, wherein an edge of the bevel is formed to face towards a center point of a curvature of the curved needle.

4. The intravenous therapy system of claim 1, wherein in response to insertion of a second length of the curved needle and a second length of the curved catheter into a patient's body, the curved needle and the curved catheter are parallel with the blood vessel.

5. The intravenous therapy system of claim 1, wherein the curved catheter is made of a polymer and thermoformed onto the curved needle.

6. The intravenous therapy system of claim 1, wherein a curvature of the curved needle and a curvature of the curved catheter are created subsequent to a straight needle being formed around a straight catheter.

7. The intravenous therapy system of claim 1, wherein in response to complete insertion of the curved needle and curved catheter, a bevel of the needle is prevented from being pressed against a wall of the blood vessel.

8. A method of manufacturing an intravenous device, comprising:
- introducing a heated metal at an extrusion die, wherein the extrusion die comprises an internal spider die, wherein the internal spider die comprises a central shaft and a funnel portion, the central shaft defining an interior diameter of a hollow tube and the funnel portion defining an outer diameter of the hollow tube;
- adjusting an exit plane of the internal spider die to be non-orthogonal to an extrusion axis of the spider die, wherein the central shaft and the funnel portion form the exit plane having a high side and a low side such that the exit plane is non-orthogonal to the extrusion axis aligned with the central shaft;
- extruding the heated metal through the extrusion die forming the hollow tube therefrom, wherein when the heated metal is extruded through the extrusion die, the hollow tube that is formed curves away from the low side towards the high side to form a curve in the hollow tube, wherein the curve in the hollow tube is between 5 and 15 degrees;
- and
- forming a catheter over the hollow tube to form a curved catheter on the hollow tube, wherein a curvature angle of the catheter is between 5 and 15 degrees.

9. The method of claim 8, wherein the metal is a stainless steel.

10. The method of claim 8, further comprising applying a heat to the catheter to relax the catheter against the outer surface of the hollow tube.

11. The method of claim 8, further comprising forming a bevel at a distal end of the hollow tube to form a sharp tip.

12. The method of claim 8, further comprising adjust an exit plane of the internal spider die during extrusion from being non-orthogonal to the extrusion axis of the spider die to being orthogonal to the extrusion axis to form a straight portion of the hollow tube along a second distance of the total length of the hollow tube.

13. The method of claim 8, further comprising annealing the hollow tube.

14. A method of manufacturing an intravenous device, comprising:
- introducing a heated metal at an extrusion die, wherein the extrusion die comprises an internal spider die, wherein the internal spider die comprises a central shaft and a funnel portion, the central shaft defining an interior diameter of a hollow tube and the funnel portion defining an outer diameter of the hollow tube;
- extruding the heated metal through the extrusion die forming the hollow tube therefrom, wherein the central shaft and the funnel portion form an exit plane that is orthogonal to an extrusion axis aligned with the central shaft, wherein when the heated metal is extruded through the extrusion die, the hollow tube that is formed is straight;
- forming a plastic catheter around an outside of the hollow tube such that the plastic catheter is coaxial with the hollow tube that is straight; and
- with a bend fixture, bending the hollow tube and the plastic catheter to form a curve in the hollow tube and the plastic catheter, wherein the curve in the hollow tube and the plastic catheter is between 5 and 15 degrees.

15. The method of claim 14, wherein the metal is a stainless steel.

16. The method of claim 14, further comprising applying a heat to the catheter to relax the catheter against the outer surface of the hollow tube.

17. The method of claim 14, further comprising annealing the hollow tube.

18. The method of claim 14, wherein an angle of the curve is between 1 and 10 degrees.

19. The method of claim 8, wherein a spacing between the funnel and the central shaft is uniform.

20. The method of claim 14, wherein a spacing between the funnel and the central shaft is uniform.

* * * * *